US006421633B1

(12) United States Patent
Heinonen et al.

(10) Patent No.: US 6,421,633 B1
(45) Date of Patent: Jul. 16, 2002

(54) DIABETES MANAGEMENT (75) Inventors: Pekka Heinonen, Espoo; Mikko Mäkipää, Helsinki, both of (FI)

(73) Assignee: Nokia Mobile Phones Ltd, Espoo (FI)

( * ) Notice: Subject to any disclaimer, the term of this patent is extended or adjusted under 35 U.S.C. 154(b) by 0 days.

(21) Appl. No.: 09/082,744

(22) Filed: May 21, 1998

(30) Foreign Application Priority Data

May 30, 1997 (FI) .................................................. 972292

(51) Int. Cl.[7] ........................... G06F 7/60; G06F 17/10; G06G 7/48; G06G 7/58
(52) U.S. Cl. ............................................. 703/11; 703/2
(58) Field of Search ....................................... 703/2, 11

(56) References Cited

U.S. PATENT DOCUMENTS

| | | | | |
|---|---|---|---|---|
| 5,415,167 A | | 5/1995 | Wilk ........................ | 128/653.1 |
| 5,701,904 A | * | 12/1997 | Simmons et al. ........... | 600/301 |
| 5,715,823 A | * | 2/1998 | Wood et al. ................ | 600/437 |
| 5,840,020 A | * | 11/1998 | Heinonen et al. ........... | 600/309 |
| 5,987,519 A | * | 11/1999 | Peifer et al. ................ | 709/230 |

FOREIGN PATENT DOCUMENTS

| | | |
|---|---|---|
| FR | 2 710 438 | 3/1995 |
| WO | WO 95/33996 | 12/1995 |

OTHER PUBLICATIONS

Mavridis et al.; "TELEMED–first results from Europe's largest broadband communications project in telemedicine"; IEEE Int. Conf. Integrated Broadband Services & Networks; pp. 126–135, Jan. 1990.*

O'Reilly et al.; "Methods of assessment of pulse oximeters"; IEE Coll. Pulse Oximetry: A critical appraisal; pp. 6/1–6/7, Jan. 1996.*

Bettini et al.; "Models of glucose disposal: estimation of glucose effectiveness with an optimal protocol"; IEEE Int. Conf. Engin. Medicine & Biol. Soc.; pp. 1828–1829, Oct. 1996.*

CAPLUS AN 1991:677054: Clin. Ter. (Rome) (1991) 136 (4)—(Abstract).

CAPLUS 1980:53726: J. Theor. Biol., (1979) 81—(Abstract).

MEDLINE AN 84209287: Diabete et Metabolisme (1984) 10 (1)—(Abstract).

MEDLINE AN 89114311; Scandinavian Journal of Clinical and Laboratory Investigation (1988) 48 (6)—(Abstract).

"Maximum Likelihood From Incomplete Data Via The EM Algorithm", Dempster et al., J. Royal Statistical Soc., B39 (1); 1–38.

"Numerical Recipes in C: The Art Of Scientific Computing", Teukolsky et al., 2$^{nd}$ ed., Cambridge University Press, 1992. (relevant pages enclosed).

"A Telemedicine Distributed Decision–Support System for Diabetes Management " Gomez et al. Dept. of Electronic Technology and Bioengineering, ETSI de Telecomunicacion, Univ. Politecnica de Madrid, Spain.

European Search Report.

* cited by examiner

*Primary Examiner*—Kevin J. Teska
*Assistant Examiner*—Hugh Jones
(74) *Attorney, Agent, or Firm*—Perman & Green, LLP (57) ABSTRACT

A method and system of predicting the level of the $HbA_{1C}$ component of glycosylated haemoglobin in a patient's blood. A mathematical model is derived which predicts the behavior of the $HbA_{1C}$ component level relative to the blood glucose level using previously measured $HbA_{1C}$ and blood glucose levels. The model is updated each time a new $HbA_{1C}$ level is measured using that new measurement and recent new blood glucose level measurements. The updated model is then applied to predict the $HbA_{1C}$ level, between measurements of that level, using measurements of blood glucose level obtained since the last $HbA_{1C}$ measurement.

23 Claims, 8 Drawing Sheets

DIABETES MANAGEMENT

FIELD OF THE INVENTION

The present invention relates to the management of diabetes and more particularly to a method and apparatus for monitoring the effectiveness of diabetes treatment.

BACKGROUND OF THE INVENTION

In the treatment of diabetes, a patient is required to regularly check his blood glucose level using a self-testing kit. By comparing the result of a self-test with the blood glucose level which he would consider normal, the patient is able to estimate the amount of insulin which should be taken in order to bring his blood glucose level back towards that normal. Self-testing kits used for this purpose have today become very sophisticated and reliable and provide an excellent means for the short term control of diabetes. However, diabetic patients can also suffer problems arising from their condition which only become apparent in the longer term. An individual blood glucose measurement obtained by a self-test provides little or no indication of the onset of such long term problems.

The basic problem which diabetic patients have relates to the transfer of sugar, contained in the blood, across cell membranes. This problem in turn makes it difficult for the body to maintain sugar levels in the blood at the correct level. Too much blood sugar (e.g. due to the patient injecting too little insulin) and the patient becomes hyperglycaemic while too little blood sugar (e.g. due to the patient injecting too much insulin) may cause the patient to become hypoglycaemic. In particular, excessive levels of sugar in the blood result in sugar combining with protein to form glycosylated protein. Glycosylated protein is substantially insoluble and gives rise to thickening of the walls of veins and arteries, and thickening of the myelination of nerves.

One particular form of glycosylated protein is glycosylated haemoglobin. As glycosylated haemoglobin tends to remain in the blood in the long term, it provides an excellent indication of the level of glycosylated protein in the blood and therefore of the effectiveness of the treatment regime which a patient has been following, as well of course as indicating how well the patient is following that regime.

Glycosylated haemoglobin is composed of three components; namely, $HbA_{1A}$, $HbA_{1B}$, and $HbA_{1C}$. The $HbA_{1C}$ level in particular is commonly measured by laboratory test in order to provide information on the long term effectiveness of diabetes treatment. The $HbA_{1C}$ level reflects the effectiveness of blood glucose treatment over the 6–8 week period preceding the $HbA_{1C}$ measurement. It has been shown that a low level of $HbA_{1C}$ in a diabetic patient's blood is a good indication that the treatment regime is effective and the risk of secondary problems related to glycosylated haemoglobin is low. The level of namely $HbA_{1C}$ in a healthy person's blood is between 4 and 6% of the total haemoglobin while in a diabetic person the level may be significantly higher (e.g. greater than 8%). It is generally sought to reduce the level of $HbA_{1C}$ in a diabetic patient's blood to between 6 and 7%.

Due to the often scarce nature of health service resources, and for the sake of convenience and practicality, the $HbA_{1C}$ level in a patient's blood is generally tested only every 3 to 4 months. However, given that the $HbA_{1C}$ level provides an indication of the effectiveness of treatment over the previous 6 to 8 weeks, long periods of ineffective treatment, and therefore damage to a patient's health, can go undetected with current testing regimes.

The article 'A Theoretical Model to Predict the Behaviour of Glycosylated Hemoglobin Levels' by Kirk W. Beach, J. theor. Biol. (1979) 81,547–561, describes a mathematical model for predicting the level of glycosylated haemoglobin from the blood glucose level. This model is however extremely crude and makes use of the simplification that the blood glucose level is either constant, changing only by way of a small number of discrete steps, or varying sinusoidally. Application of the model to a real patient necessarily involves a great over-simplification of the behavior of blood glucose levels.

It is an object of the present invention to overcome or at least mitigate disadvantages of known diabetes management techniques.

It is a further object of the present invention to provide a method and apparatus for providing a substantially continuous estimate of glycosylated haemoglobin component levels.

SUMMARY OF THE INVENTION

According to a first aspect of the present invention there is provided a method of predicting the level of a glycosylated haemoglobin component in a patient's blood using previously measured blood glucose and glycosylated haemoglobin component levels, the method comprising:

deriving a mathematical model of the behavior of the glycosylated haemoglobin component level relative to the blood glucose level using previously measured levels;

updating the model when a new glycosylated haemoglobin component level is measured using that new measurement and recent new blood glucose level measurements; and applying the mathematical model to predict the glycosylated haemoglobin component level, between measurements of that level, using measurements of blood glucose level obtained since the last glycosylated haemoglobin component measurement.

Typically, blood glucose level measurements are made at a considerably higher frequency than glycosylated haemoglobin component measurements. The method of the present invention may therefore be used to predict the current glycosylated haemoglobin component level in a patient's blood using blood glucose level measurements obtained since the last glycosylated haemoglobin component level measurement. As the model is updated each time a new $HbA_{1C}$ measurement is made, the model is capable of tracking changes in the physiology of the patient which cause the behavior of the $HbA_{1C}$ level to change with respect to the blood glucose level. Changes in the blood glucose measurement pattern, i.e. the times at which the patient makes blood glucose measurements, can also be accounted for.

Preferably, the mathematical model is a parametric model or a semi-parametric model, where the model is defined by one or more model coefficients and a model equation which relate blood glucose level to the glycosylated haemoglobin component level. More preferably, the model equation relates the glycosylated haemoglobin component level to one or more parameters which describe, at least in part, the behavior (e.g. distribution) of the blood glucose level over a preceding, relatively short, time interval.

The model equation may be a linear equation in which case said model coefficients are the linear coefficients of the equation. The linear equation is of the form:

$$y = p_1 h_1 + p_2 h_2 + \ldots p_q h_q + c$$

where y is the predicted glycosylated haemoglobin level, p are the linear model coefficients, h are the parameters which describe blood glucose level behavior, and c is a constant.

Preferably, the behavior of the blood glucose level over said short time intervals may be described using one or more gaussian functions which model the distribution of blood glucose level measurements. Said one or more parameters (h) may be chosen from the mean, variance, and amplitude of the gaussian function(s) or may be derived therefrom.

In the case of a parametric or semi-parametric model, the model may be updated following each glycosylated haemoglobin component level measurement by recalculating said model coefficients (p). In an alternative embodiment of the present invention, the coefficients of the parametric model are adapted following each new glycosylated haemoglobin level measurement using an adaptive algorithm. One suitable adaptive algorithm is Widrows algorithm. Such adaptive algorithms are arranged to reduce the error between the predicted glycosylated haemoglobin level and the measured glycosylated haemoglobin level.

The glycosylated haemoglobin component predicted using the method of the above first aspect of the present invention is one of $HbA_{1A}$, $HbA_{1B}$, and $HbA_{1C}$. Preferably however, the predicted component is $HbA_{1C}$.

The method of the above first aspect of the present invention may comprise:

transmitting measured glucose levels via a wireless data transmission link from a remote station, available to the patient, to a central data processing station;

carrying out said steps of deriving the mathematical model, updating the model, and predicting the glycosylated haemoglobin component at the central processing station using the transmitted measurements and previous measurement data stored at the central station; and transmitting predicted glycosylated haemoglobin component levels back to the remote station via the wireless data transmission link.

Preferably, the remote station is a mobile telephone or a two-way pager whereby the wireless data transmission link is provided by a mobile telephone network. For example, the telephone network may be a GMS network and the data may be transmitted by the short message service (SMS). It is to be understood that the term 'mobile telephone' as used here refers to any portable device which utilizes wireless telephonic communication including conventional cellular telephones and combined cellular telephone/personal data assistant (PDA) devices.

Alternatively, the method may comprise carrying out all of the steps of the method of the above first aspect of the invention in a portable monitoring device.

It will be appreciated that the method of the present invention may be applied to blood taken from a human or animal patient.

According to a second aspect of the present invention there is provided a method of predicting the level of a glycosylated haemoglobin component in a patient's blood, the method comprising the steps of:

transmitting a blood glucose measurement from a remote station to a central processing station;

predicting at the central station a glycosylated haemoglobin component level for the patient's blood using said transmitted measurement and a mathematical model of the glycosylated haemoglobin component level relative to blood glucose level; and transmitting the predicted glycosylated haemoglobin component level from the central station to the remote station.

According to a third aspect of the present invention there is provided a system for predicting the level of a glycosylated haemoglobin component in a patient's blood using previously measured blood glucose and glycosylated haemoglobin component levels, the system comprising:

means for deriving a mathematical model of the behavior of the glycosylated haemoglobin component level relative to the blood glucose level using previously measured levels, and for updating the model when a new glycosylated haemoglobin component level is measured using that new measurement and recent new blood glucose level measurements; and memory means for storing said model and/or the updated model and measured blood glucose and glycosylated haemoglobin component levels;

means for applying the mathematical model to predict the glycosylated haemoglobin component level, between measurements of that level, using measurements of blood glucose level obtained since the last glycosylated haemoglobin component measurement.

In a preferred embodiment of the system of the above third aspect of the present invention, said means for deriving and applying and said memory means are provided by a central computer, the system further comprising a mobile telephone or two-way pager for conveying measurement data to the central computer via a wireless data transmission link. The system may be further arranged to convey predicted glycosylated haemoglobin component levels from the central station to the mobile telephone or two-way pager.

For a better understanding of the present invention and in order to show how the same may be carried into effect reference will now be made, by way of example, to the accompanying drawings, in which:

DETAILED DESCRIPTION

Figure 1:
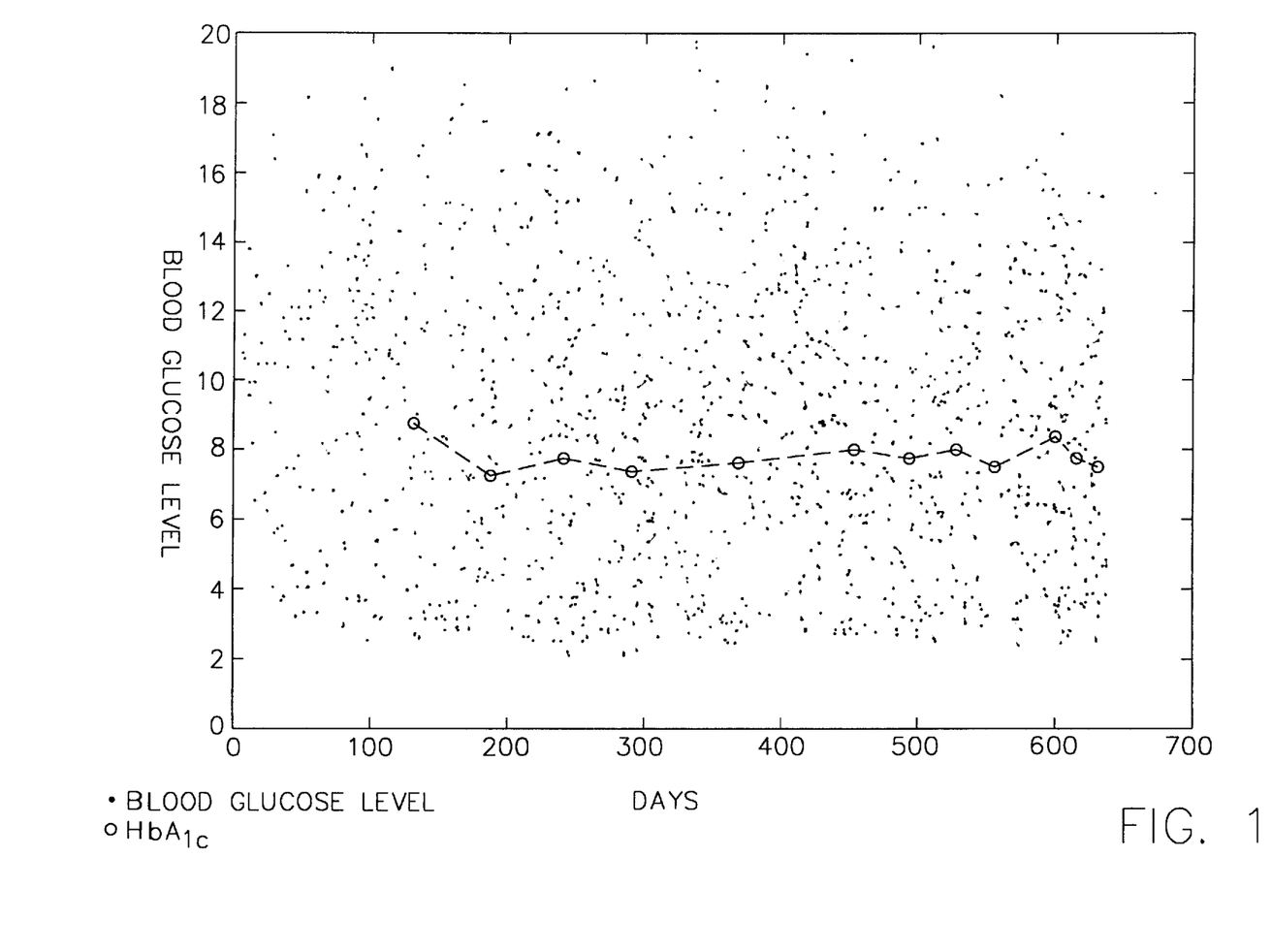
FIG. 1 shows $HbA_{1C}$ level measurements together with blood glucose level measurements obtained from a diabetic patient over a period of 640 days.
Figure 2A:
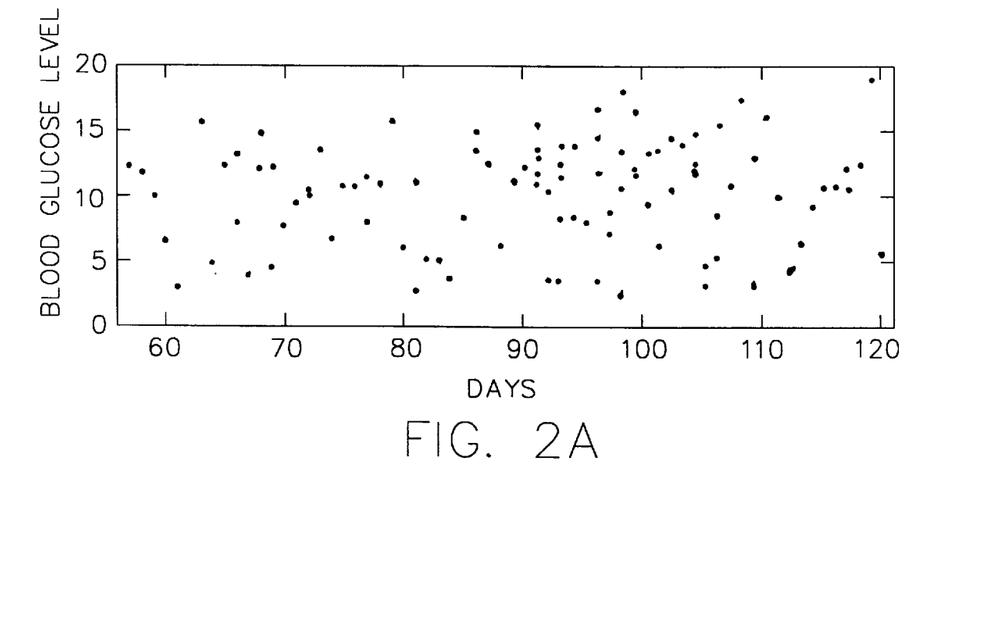
FIGS. 2A to 2D show respective sets of blood glucose level measurements, extracted from the measurements shown in FIG. 1, for periods preceding four $HbA_{1C}$ level measurements.
Figure 2B:
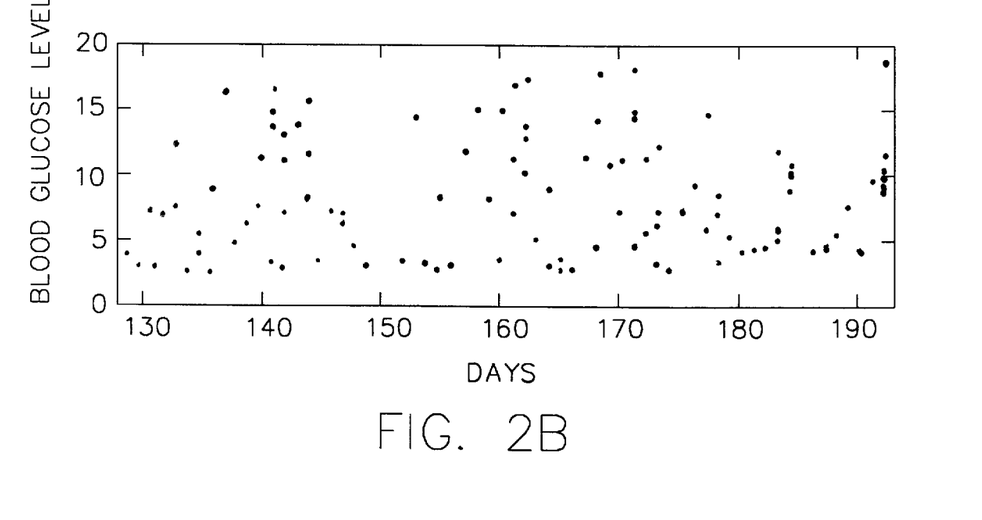
Figure 2C:
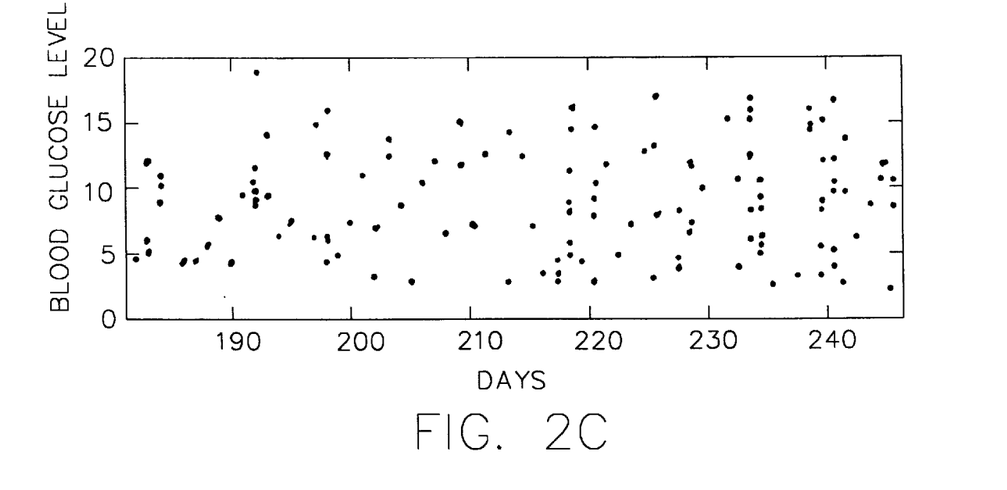
Figure 2D:
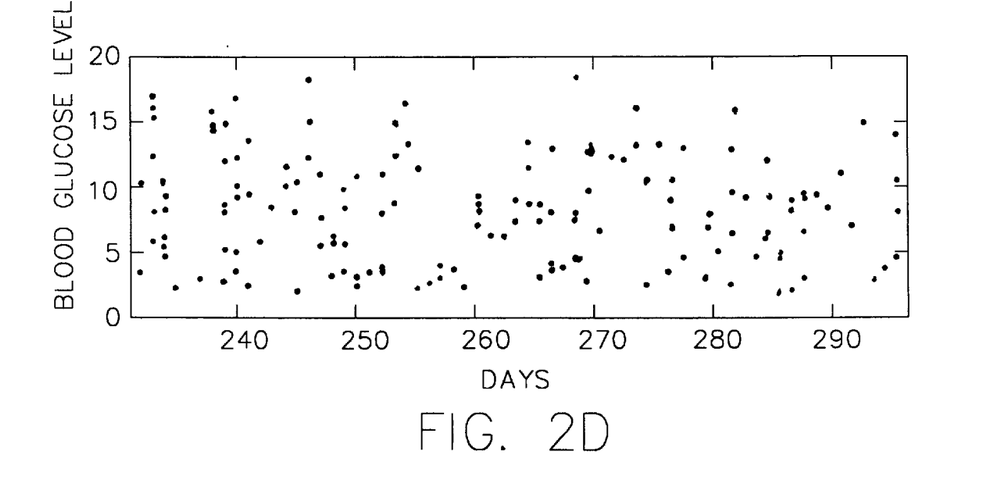
Figure 3A:
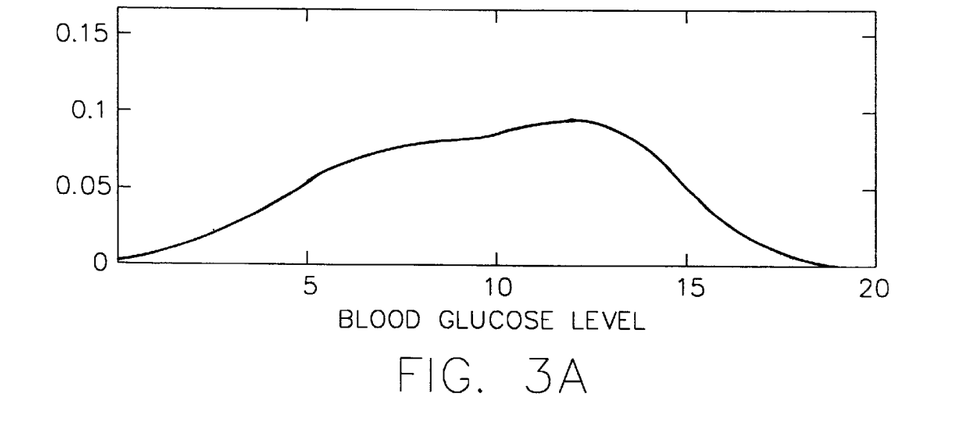
FIGS. 3A to 3D show respectively predicted blood glucose level distributions for each of the measurement windows of FIGS. 2A to 2D.
Figure 3B:
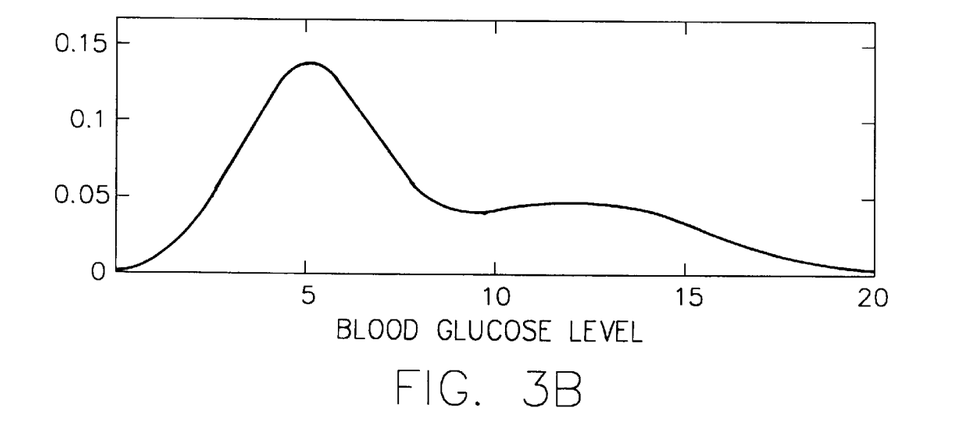
Figure 3C:
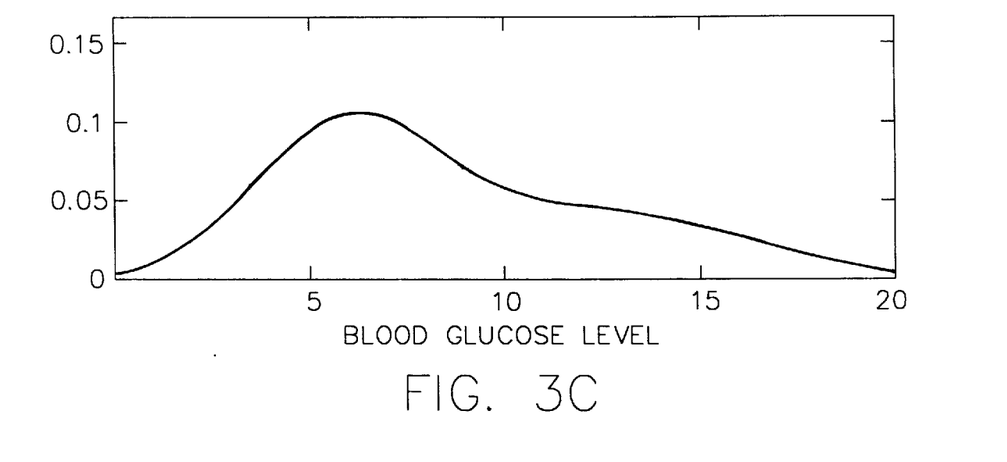
Figure 3D:
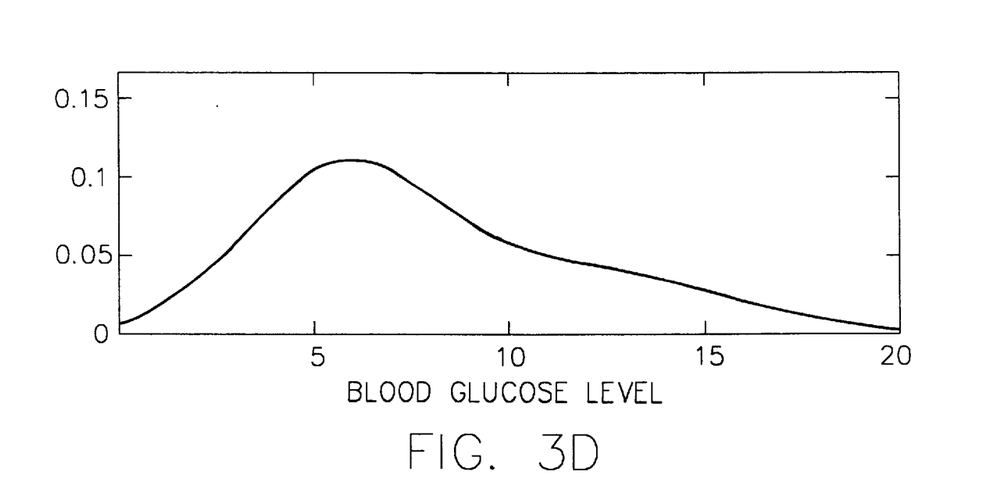

The method described below for predicting $HbA_{1C}$ levels in the blood of a patient is illustrated using actual blood glucose and $HbA_{1C}$ measurements obtained from a human patient. FIG. 1 shows the measured blood glucose and $HbA_{1C}$ levels plotted against time (measured in days) over a period of 640 days. As discussed above, $HbA_{1C}$ measurements are typically made at relatively infrequent intervals (every 12 to 16 weeks) while blood glucose level measurements are made much more frequently (typically two to five times a day).

Let Y be the set of N available $HbA_{1C}$ measurements $y_n$ shown in FIG. 1, where $Y=\{Y_1 \ldots Y_N\}$ and each measurement corresponds to a measurement time $t=T_n$, (n=1 to N). Similarly, let X be the set of M available blood glucose measurements $x_m$ also shown in FIG. 1, where $X=\{x_1 \ldots x_M\}$ and each measurement corresponds to a measurement time $t=t_m$, (m=1 to M). The set of blood glucose measurements X is divided into sub-sets $X_n$, each sub-set being associated with the corresponding $HbA_{1C}$ measurement $Y_n$, and containing those values obtained in the period $t>T_{n-}65$ days to $T_N$. It is noted that when the interval between consecutive $HbA_{1C}$ is less than 65 days, adjacent sub-sets $X_n$ will overlap. For the data of FIG. 1, with twelve $HbA_{1C}$ measurements, twelve sub-sets of blood glucose measurements are obtained, the first four of these being shown in FIGS. 2A to 2D for the purpose of illustration.

A suitable semi-parametric model is applied to each sub-set of blood glucose level measurements $X_n$, to model the distribution of the measurements within the set (i.e. to model the probability density function). The model is chosen to have a relatively small number of parameters. In the present example, the distribution of each sub-set $X_n$, is modeled using the sum of a pair of gaussian functions:

$$P(l)=kG(l|\mu_1,\sigma_1^2)+(1-k)G(l|\mu_2,\sigma_2^2) \quad (1)$$

where k is a coefficient and $0 \leq k \leq 1$, l is the blood glucose level, and the gaussian function G has the form:

$$G(l) = \frac{1}{2\pi\sigma^2}\exp\left\{-\frac{(l-\mu)^2}{2\sigma^2}\right\} \quad (2)$$

The means $(\mu_1,\mu_2)$ and variances $(\sigma_1^2,\sigma_2^2)$, of the gaussian functions, as well as the coefficient k, are obtained using the expectation-maximization algorithm (see Dempster A. P., Laird N. M., and Rubin, D. B. (1977); 'Maximum Likelihood from Incomplete Data via the EM Algorithm'; J. Royal Statistical Soc.; B 39 (1); 1–38). The modeled distribution for each of the sub-sets of blood glucose measurements are shown in FIGS. 3A to 3D.

Each model can be represented by a parameter vector $\Theta_n\{\mu_{n1},\mu_{n2},\sigma_{n1}^2,\sigma_{n2}^2,k\}$. A suitable combination of parameters is selected from the parameter vector $\Theta_n$ and is used to form a model vector $h_n$, at time $T_n$. In the present example the parameters $\mu_1,\mu_2,\sigma_1^2$ and a constant 1 are selected, corresponding respectively to $h_{n1},h_{n2},h_{n2},h_3$ and $h_{n4}$ of the model vector. The model vectors $h_n$ and the measured $HbA_{1C}$ levels $y_n$ are used to form the rows of a model specification matrix H and an observation vector z respectively and the linear problem $z=Hp$ constructed, where p is a regression coefficient vector. This problem can be more fully written as the matrix equation:

$$\begin{bmatrix} y_1 \\ y_2 \\ \vdots \\ y_N \end{bmatrix} = \begin{bmatrix} h_{11} & h_{12} & h_{13} & h_{14} \\ h_{21} & h_{22} & h_{23} & h_{24} \\ \vdots & \vdots & \vdots & \vdots \\ h_{N1} & h_{N2} & h_{N3} & h_{N4} \end{bmatrix} \begin{bmatrix} p_1 \\ p_2 \\ p_3 \\ p_4 \end{bmatrix} \quad (3)$$

An estimate of the regression coefficient vector p can be determined from:

$$\hat{p}=H^{-1}z \quad (4)$$

where $H^{-1}$ is the inverse of the matrix H (or pseudo inverse in the case that H is not square or is singular) and can be obtained using a singular value decomposition technique (Press, W. H. Teukolsky, S. A. Vetterling, W. T. Flannery, B. P. 1992, 'Numerical Recipes in C: The Art of Scientific Computing', 2nd ed. Cambridge University Press). The estimated regression coefficient vector $\hat{p}$ can then be used to predict a future $HbA_{1C}$ level $Y_{N+1}$ from the model vector $h_{N+1}$, derived from the sub-set of blood glucose measurements $X_{N+1}$, i.e.:

$$Y_{N+1}=p_1h_{N+1,1}+p_2h_{N+1,2}+p_3h_{N+1,3}+p_4h_{N+1,4}. \quad (5)$$

Figure 4:
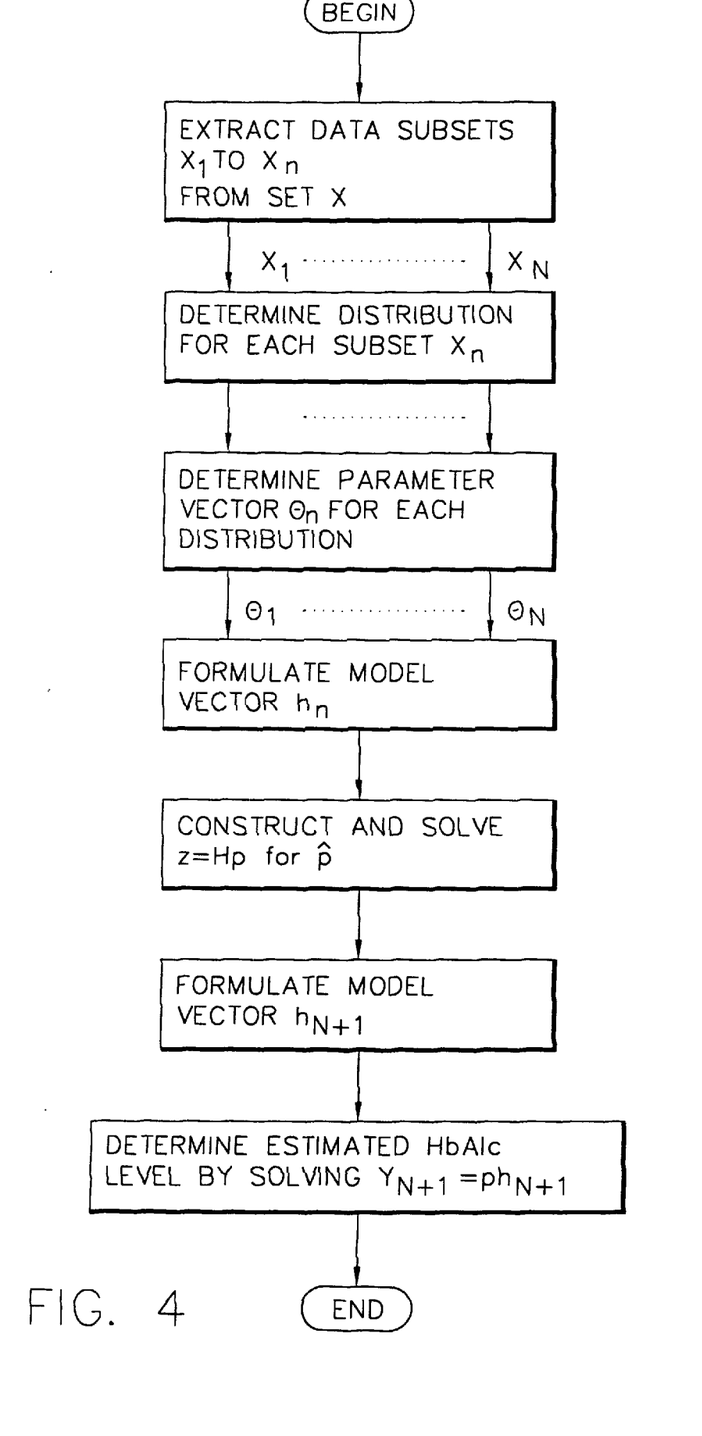
FIG. 4 is a flow chart illustrating a method used to predict $HbA_{1C}$ levels.

FIG. 4 is a flow diagram outlining the main steps of this method of predicting $HbA_{1C}$ levels.

As has been explained above, changes in the physiology of a patient are likely to change the behavior of the $HbA_{1C}$ level with respect to blood glucose level. It is therefore important that the coefficients of the regression coefficient vector $\hat{p}$ be updated regularly. This can be achieved by recalculating the vector $\hat{p}$ every time a new $HbA_{1C}$ measurement is made. Typically, for a patient with no previous records, the regression coefficient vector is first derived using data obtained from a number of other patients. Each time a new $HbA_{1C}$ measurement is made, the new $HbA_{1C}$ measurement, together with the blood glucose measurements obtained since the last $HbA_{1C}$ measurement, is used in the recalculation of the regression coefficient vector. Assuming that the value of N is maintained constant by removing the earliest obtained measurements in turn, after N $HbA_{1C}$ measurements have been obtained from the subject patient, the estimated regression coefficient vector will be derived solely from measurements made on the subject patient.

Figure 5:
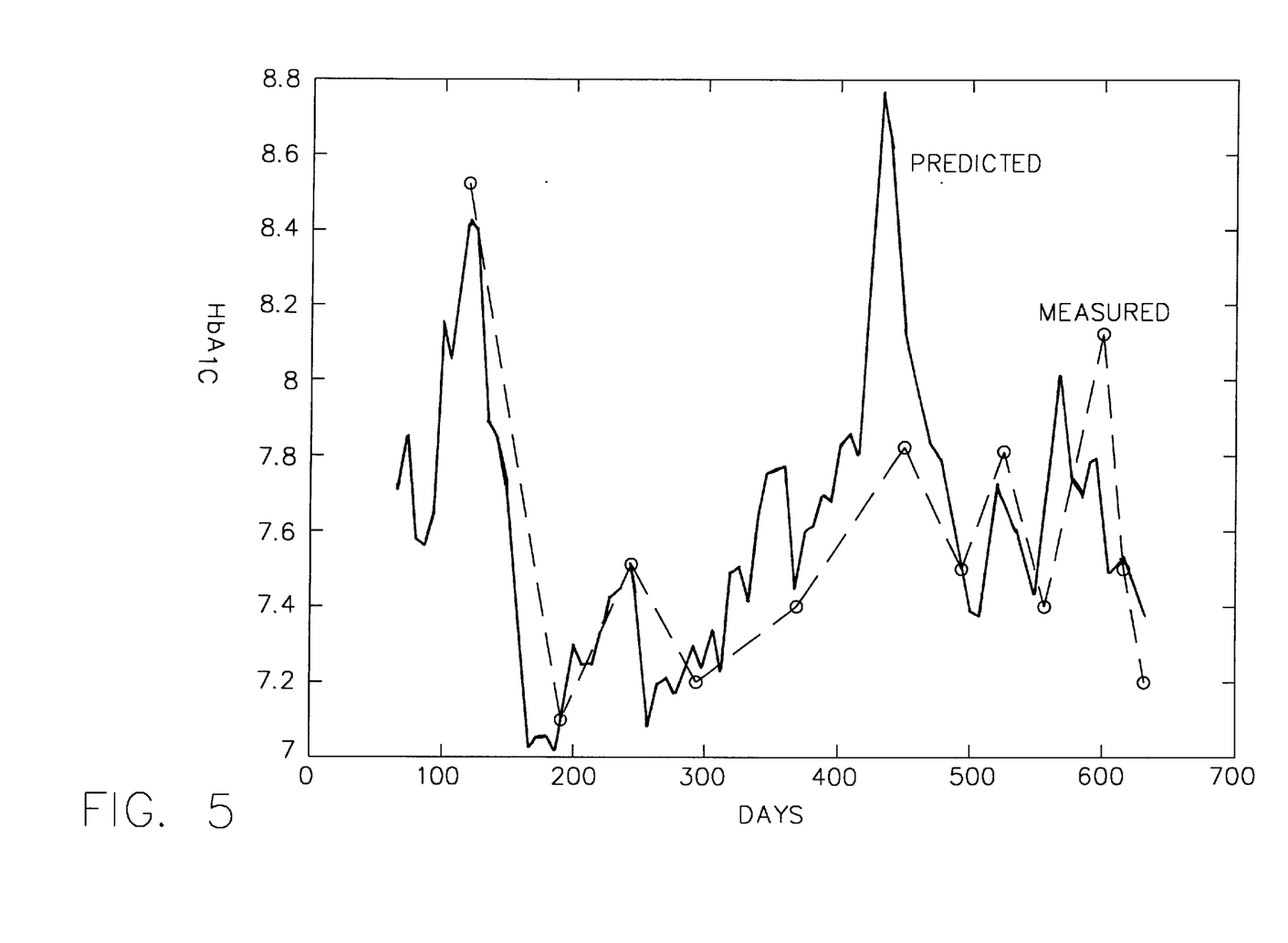
FIG. 5 shows measured $HbA_{1C}$ levels of FIG. 1 together with predicted $HbA_{1C}$ levels.

In order to improve the accuracy with which the $HbA_{1C}$ level can be predicted, and more particularly to avoid biasing of the result by rogue measurements, an estimated regression coefficient vector $\hat{p}$ is in fact obtained for N different data sets, omitting in turn each of the elements $y_1$ to $y_N$ of the above matrix equation together with the corresponding row of the matrix H. The mean of the estimated regression coefficient vectors is then obtained after removing the top and bottom 10% of each of the vector components. For the data set shown in FIG. 1, the final estimated regression coefficient vector is the trimmed mean of twelve estimated vectors $\hat{p}$. The coefficients of this final regression coefficient vector can then be used to predict the current $HbA_{1C}$ level using equation (5) above. FIG. 5 shows $HbA_{1C}$ levels predicted using a model obtained with this method together with the measured $HbA_{1C}$ levels used to formulate the model (and as shown in FIG. 1). It can be seen that the predicted values closely follow the measured values.

Further improvements in prediction accuracy may be achieved by increasing the number of parameters p, by increasing the size of the model vector $h_n$, e.g. to additionally include $\delta_2$. Alternatively, a set of $HbA_{1C}$ estimates may be made using a corresponding set of parametric models, each model being obtained using a different set of parameters, e.g. $\mu_1,\mu_2,\sigma_1^2,k$ or $\mu_1,\mu_2,\sigma_2^2,k$. Accuracy may also be increased by appropriately transforming (e.g. log, exponential) one or more of the parameters.

It is well known that blood glucose levels in a patient fluctuate periodically according to the time of day and more particularly according to whether or not the patient has just eaten. It may therefore be more accurate to separately model blood glucose levels for different times of day. This technique requires the separation of all blood glucose levels into separate sets. There might, for example, be nine sets, i.e. measurements made before and after breakfast, lunch, dinner, and evening snack. For each set j, a set of parameter vectors $\Theta_n^j$ is obtained, where n=1 . . . N. Again, for each value of n, a set of suitable parameters are selected to form the model vector $h_n$. The estimated regression coefficient vector $\hat{p}$ can then be obtained as described above.

Given that the calculation of the regression coefficient vector may involve a considerable amount of stored data (e.g. up to two years of measurement data), and hence present a considerable degree of computational complexity, it is desirable to store the measurement data and perform computations at a central data processing unit available to many patients. In addition, this arrangement improves data security and, importantly, allows the algorithm by which $HbA_{1C}$ levels are predicted to be easily and quickly updated, should that prove necessary.

Figure 6:
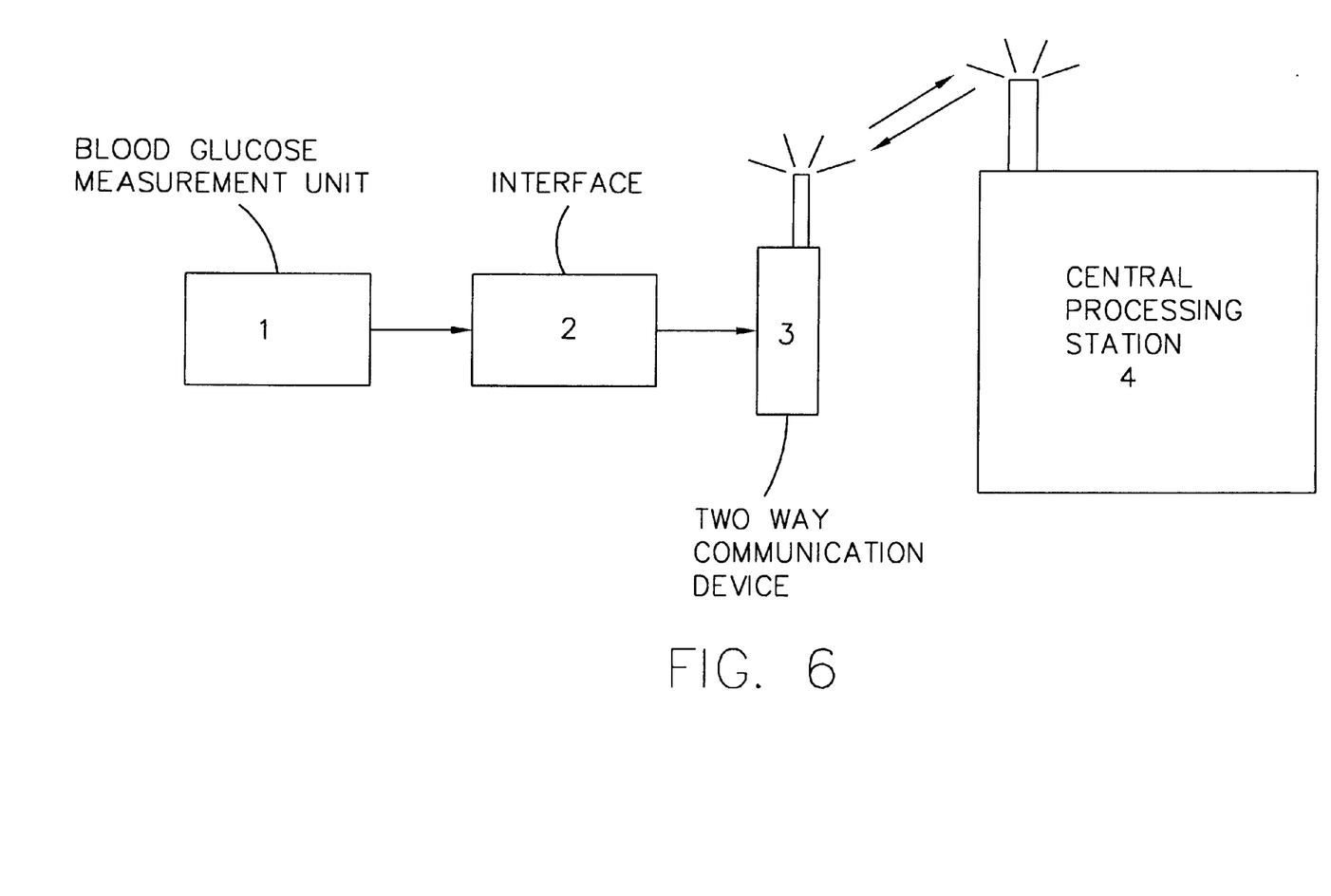
FIG. 6 illustrates schematically apparatus for implementing the method of FIG. 5.

FIG. 6 illustrates a diabetic management system for predicting the level of a glycosylated haemoglobin component in a patient's blood using previously measured blood glucose and glycosylated haemoglobin component levels. The system comprises: means for deriving a mathematical model of the behavior of the glycosylated haemoglobin component level relative to the blood glucose level using previously measured levels, and for updating the model when a new glycosylated haemoglobin component level is measured using that new measurement and recent new blood glucose level measurements; memory means for storing said model and the updating model and measured blood glucose and glycosylated haemoglobin component levels; and means for applying the mathematical model to predict the glycosylated haemoglobin component level, between measurements of that level, using measurements of blood glucose level obtained since the last glycosylated haemoglobin component measurement. Said means for deriving and applying and said memory means are provided by a central computer. The system further comprises a mobile telephone or two-way pager, for conveying measurement data to the central computer via a wireless data transmission link and a mobile telephone or two-way pager, for conveying measurement data to the central computer via a wireless data transmission link. A blood glucose measurement unit is coupled to the mobile telephone or two-way pager for transmitting blood glucose level measurements to the mobile telephone or two-way pager. The system is arranged to convey predicted glycosylated haemoglobin component levels from the central station to the mobile telephone or two-way pager.

Each patient in the system is provided with a portable electronic blood glucose measurement unit 1 of known type. This unit is modified for coupling measured blood glucose levels via an interface 2, for example a notebook computer or PC, to a mobile telephone 3. The measurement data is then transmitted via the mobile telephone network to a central data processing station 4 of the type described above. Based on recently received blood glucose measurements, and a precalculated regression coefficient vector, the central processing station 4 estimates the patient's $HbA_{1C}$ level. The regression coefficient vector can be updated each time a $HbA_{1C}$ measurement is made on the patient either using data entered directly into the central data processing station or transmitted to it from, for example a doctor's surgery. The predicted $HbA_{1C}$ level can be almost immediately transmitted back to the patient's mobile phone 3, via the telephone network, where it can be displayed on the phone 3 or the interface 2. By integrating the functions of the mobile phone 3, the interface 2, and the measurements unit 1, the patient can be provided with a truly portable $HbA_{1C}$ level monitoring system.

The method comprises: transmitting measured glucose levels via a wireless data transmission link from a remote station, available to the patient, to a central data processing station; the mathematical model is derived and updated and the glycosylated haemoglobin component is predicted at the central processing station using the transmitted measurement and previous measurement data stored at the central station. The predicted glycosylated haemoglobin component level is transmitted back to the remote station via the wireless data transmission link. A method of predicting the level of a glycosylated haemoglobin component in a patient's blood comprises the steps of transmitting a blood glucose measurement from a remote station to a central processing station; predicting at the central station a glycosylated haemoglobin component level for the patient's blood using the transmitted measurement and a mathematical model of the glycosylated haemoglobin component level relative to blood glucose level. The predicted glycosylated haemoglobin component level is transmitted from the central station to the remote station.

It will be appreciated by the skilled person that other modifications may be made to the above described embodiment without departing from the scope of the present invention. For example, the probability density function of each set of blood glucose levels $X_n$ may be modeled using one or more gamma functions as an alternative to gaussian functions.

What is claimed is:

1. A method of predicting a level of a glycosylated haemoglobin component in a patient's blood using previously measured blood glucose levels and previously measured glycosylated haemoglobin component levels, the method comprising the steps of:

deriving a mathematical model of the behavior of the glycosylated haemoglobin component level relative to a newly measured blood glucose level using previously measured blood glucose levels;

updating the model when a new glycosylated haemoglobin component level is measured using the new glycosylated haemoglobin component level measurement and recent new blood glucose level measurements obtained since the new glycosylated haemoglobin component level measurement; and applying the mathematical model to predict the glycosylated haemoglobin component level, between measurements of the glycosylated haemoglobin component level, using measurements of the blood glucose level obtained since a last glycosylated haemoglobin component measurement.

2. A method according to claim 1, wherein the mathematical model is a parametric model or a semi-parametric model and is defined by one or more model coefficients and a model equation which relate blood glucose level to the glycosylated haemoglobin component level.

3. A method according to claim 2, wherein the model equation relates the glycosylated haemoglobin component level to one or more parameters which describe behavior of the blood glucose level over a preceding time interval.

4. A method according to claim 3, wherein the model equation is a linear equation having the form:

$$y = p_1 h_1 + p_2 h_2 + \ldots + p_q h_q + c$$

where y is the predicted glycosylated haemoglobin level, p are the linear model coefficients, h are the parameters which describe blood glucose level behavior, and c is a constant.

5. A method according to claim 3, wherein the behavior of the blood glucose level over said preceding time intervals as described using one or more parametric functions which model the distribution of blood glucose level measurements and said one or more parameters (h) are selected from or derived from the parameters defining these functions.

6. A method according to claim 5, wherein the one or more functions are gaussian functions and said one or more parameters (h) are chosen from or are derived from the mean, variance, and amplitude of the gaussian function(s).

7. A method according to claim 2, wherein the model is updated following a glycosylated haemoglobin component level measurement by recalculating said model coefficients (p).

8. A method according to claim 2, wherein the coefficients of the parametric model are adapted following a new glycosylated haemoglobin level measurement using the mathematical model.

9. A method according to claim 1, wherein the glycosylated haemoglobin component predicted is $HbA_{1C}$.

10. A method according to claim 1 and comprising:
transmitting measured glucose levels via a wireless data transmission link from a remote station, available to the patient, to a central data processing station;
carrying out said steps of deriving the mathematical model, updating the model, and predicting the glycosylated haemoglobin component at the central processing station using the transmitted measurements and previous measurement data stored at the central station; and
transmitting predicted glycosylated haemoglobin component levels back to the remote station via the wireless data transmission link.

11. A method according to claim 10, wherein the remote station is a mobile telephone or a two-way pager whereby the wireless data transmission link is provided by a mobile telephone network.

12. A method of predicting the level of a glycosylated haemoglobin component in a patent's blood using previously measured blood glucose levels and previously measured glycosylated haemoglobin component levels, the method comprising the steps of:
transmitting a blood glucose measurement from a remote station to a central processing station;
predicting at the central station a glycosylated haemoglobin component level for the patient's blood using said transmitted measurement and a mathematical model of the glycosylated haemoglobin component level relative to blood glucose level; and
transmitting the predicted glycosylated haemoglobin component level from the central station to the remove station.

13. A system for predicting the level of a glycosylated haemoglobin component in a patient's blood using previously measured blood glucose and glycosylated haemoglobin component levels, the system comprising:
means for deriving a mathematical model of the behavior of the glycosylated haemoglobin component level relative to the blood glucose level using previously measured levels, and for updating the model when a new glycosylated haemoglobin component level is measured using that new measurement and recent new blood glucose level measurements;
memory means for storing said model and the updated model and measured blood glucose and glycosylated haemoglobin component levels; and
means for applying the mathematical model to predict the glycosylated haemoglobin component level obtained since the last glycosylated haemoglobin component measurement.

14. A system according to claim 13, wherein said means for deriving and applying and said memory means are provided by a central computer.

15. A system according to claim 14 and comprising a blood glucose measurement unit coupled to the mobile telephone or two-way pager for transmitting blood glucose level measurements to the mobile telephone or two-way pager.

16. A system according to claim 14 and which is arranged to convey predicted glycosylated haemoglobin component levels from the central station to the mobile telephone or two-way pager.

17. A system according to claim 13 further comprising a mobile telephone or a two-way pager adapted to convey the measured glycosylated haemoglobin component level and the measured blood glucose level to a central computer via a wireless data transmission link.

18. A system for predicting a glycosylated haemoglobin component level of a patient's blood comprising:
a blood glucose measurement unit;
a communication device coupled to the blood glucose measurement unit via an interface, the interface adapted to transmit a newly measured blood glucose level to the communication device for transmission; and
a central processing station adapted to receive the transmission of the newly measured blood glucose level from the communication device and estimate the glycosylated haemoglobin component level in the patient's blood using the newly measured blood glucose level, at least one prior glycosylated haemoglobin component level measurement and a precalculated regression coefficient vector.

19. The system of claim 18 wherein the central processing station comprises:
a computer device adapted to derive a mathematical model of a behavior of the glycosylated haemoglobin component level of the patient's blood relative to the newly measured blood glucose level and at least one previously measured glycosylated haemoglobin component level, the mathematical model including the regression coefficient vector; and
a computer device adapted to update the derived model when a new glycosylated haemoglobin component level is measured.

20. The system of claim 18 wherein the communication device is a mobile phone.

21. The system of claim 19 wherein the central processing system is adapted to apply the mathematical model to blood glucose measurements made between actual measurements of the patient's glycosylated haemoglobin component level.

22. The system of claim 19 wherein the central data processing system is adapted to transmit the estimated glycosylated haemoglobin component level back to the patient via the communication device.

23. The system of claim 18 wherein the central processing station is further adapted to store a mathematical model, including the regression coefficient vector, of the behavior of the glycosylated haemoglobin component level of the patient's blood relative to the newly measured blood glucose level and at least one previously measured glycosylated haemoglobin component level.

* * * * *